(12) United States Patent
Björck et al.

(10) Patent No.: US 6,843,999 B1
(45) Date of Patent: Jan. 18, 2005

(54) STREPTOCOCCAL ABC TRANSPORTER PROTEIN

(75) Inventors: Lars Björck, Lund (SE); Robert Janulczyk, Lund (SE)

(73) Assignee: Actinova Limited, Cambridge (GB)

( * ) Notice: Subject to any disclaimer, the term of this patent is extended or adjusted under 35 U.S.C. 154(b) by 0 days.

(21) Appl. No.: 09/869,677

(22) PCT Filed: Dec. 30, 1999

(86) PCT No.: PCT/GB99/04445

§ 371 (c)(1),
(2), (4) Date: Jan. 8, 2002

(87) PCT Pub. No.: WO00/40729

PCT Pub. Date: Jul. 13, 2000

(30) Foreign Application Priority Data

Dec. 31, 1998 (GB) ............................................... 9828880

(51) Int. Cl.⁷ ................................................ A61K 39/09

(52) U.S. Cl. ................................ 424/244.1; 424/185.1; 424/190.1; 530/300; 530/350

(58) Field of Search ................................. 530/350, 300; 124/244.1, 185.1, 190.1

(56) References Cited

U.S. PATENT DOCUMENTS 5,422,427 A * 6/1995 Russell et al.
5,854,416 A 12/1998 Sampson et al. .......... 536/23.7

OTHER PUBLICATIONS

Embl Database Entry Accession No. M63481; M37189, Mar. 22, 1991.

Dintilhac and Claverys, "The adc locus, which affects competence for genetic transformation in *Streptococcus pneumoniae*, encodes an ABC transporter with a putative lipoprotein homologous to a family of streptococcal adhesions," *Res. Microbiol. 148*:119–131,1997.

Ganeshkumar et al., "Nucleotide sequence of a gene coding for a saliva–binding protein (SsaB) from *Streptococcus sanguis* 12 and possible role of the protein in coaggregation with actinomyces," *Infection and Immunity 59*(3):1093–1099, Mar. 1991.

Janulczyk et al., "Identification and characterization of a *Streptococcus pyogenes* ABC transporter with multiple specificity for metal cations," *Molecular Microbiology 34*(3):596–606, 1999.

* cited by examiner

*Primary Examiner*—Jennifer E. Graser
(74) *Attorney, Agent, or Firm*—Popovich, Wiles & O'Connell, P.A.

(57) ABSTRACT

A polypeptide suitable for use in vaccination against Streptococcal infections comprises: a) the amino acid sequence of SEQ ID No 1; b) a variant of (a) which is capable of binding an anti-MtsA antibody; or (c) a fragment of (a) or (b) of at least 6 amino acids in length which is capable of binding an anti-MtsA antibody. A vaccine composition comprises: a) the amino acid sequence of SEQ ID No 1; b) a variant of (a) which is capable of generating an immune response to a Streptococcal; or (c) a fragment of (a) or (b) of at least 6 amino acids in length which is capable of generating an immune response against a *Streptococcus*.

14 Claims, 4 Drawing Sheets

STREPTOCOCCAL ABC TRANSPORTER PROTEIN

FIELD OF THE INVENTION

This invention relates to a novel protein which forms part of an ABC transporter of S. pyogenes. The invention also relates to a *streptococcus* vaccine composition comprising this protein or fragments thereof.

BACKGROUND OF THE INVENTION

*Streptococcus pyogenes*, group A *Streptococcus*, is a common human pathogen which causes a variety of diseases such as pharingitis, impetigo, scarlatina and erysipelas. More severe infections caused by this organism are necrotizing fasciitis and streptococcal toxic shock like syndrome.

The superfamily of ABC (ATP-binding cassette) transporters comprise many different systems in procaryotes and eukaryotes. This diverse group of transporters serve many roles including transport of nutrients, translocation of signal molecules and chemotaxis. The general principle of ABC transport includes transportation of a ligand through two integral membrane domains forming a pore, with accompanying ATP hydrolysis by two nucleotide-binding domains associated with the cytoplasmic side of the pore.

In bacteria, the translocation of ligands is preceded by interaction with an accessory component, the periplasmic binding protein. This protein binds the ligand with higher affinity, and then interacts with the integral membrane components by releasing the ligand and allowing subsequent transport. In gram-positive bacteria, the binding protein homologue is a lipoprotein attached to the cell membrane by a $NH_2$-terminal lipid moiety. Little is known about the ABC transporters in gram-positive bacteria. In particular, the interaction between the lipid protein component and the integral membrane component is unclear.

A number of recent studies have looked at an ABC transporter family in *Streptococcus* species. Examples are Correia et al Infect. Immun (1996) 64(6) 2114–2121; Fenno et al Mol. Microbiol. (1995) 15(5) 849–863; Lowe et al Infect. Immun (1995) 63(2) 703–706; Kolenbrander et al Infect. Immun (1994) 62(10) 4469–4480 and Sampson et al Infect. Immun (1994) 62(1) 319–324.

The genes encoding the ABC transporter form an operon consisting of three genes. The putative proteins encoded by these genes are a hydrophobic membrane protein, a nucleotide binding protein and a lipid protein. The operon has been sequenced in a number of important disease causing organisms such as *S.pneumoniae, Enterococcus faecalis, S.sanguis* and *S.parasanguis* as well as in commensal bacteria such as *S.gordonii* and *Streptococcus crista*. As well as playing a role in transport, the ABC transporter has also been related to bacterial virulence and may mediate bacterial coaggregation, adhesion to host cells, saliva pellicle components and fibrin clots.

SUMMARY OF THE INVENTION

The applicants have now identified a new protein of *S.pyogenes* comprising the lipoprotein of an ABC transporter. This protein is herein referred to as the SmtA protein or MtsA. The *S.pyogenes* operon is atypically organised and the polycistronic transcription is attenuated, in contrast to the previously described systems. The lipoprotein can be solubilized from the bacterial surface by proteolytic cleavage which indicates the presence of a flexible hinge region between the $NH_2$-terminal lipid moiety and a more compact globular fold. This lipoprotein and fragments thereof can be used in streptococcal vaccine compositions and in particular against *S.pyogenes*.

In a first aspect, the invention provides a polypeptide which comprises:
(a) the amino acid sequence of SEQ ID NO 1,
(b) a variant of (a) which is capable of binding an anti-MtsA antibody, or
(c) a fragment of (a) or (b) of at least 6 amino acids in length which is capable of binding to an anti-MtsA antibody.

In another aspect, the invention relates to a vaccine composition comprising a polypeptide which comprises:
(a) the amino acid sequence of SEQ ID NO 1,
(b) a variant of (a) which is capable of generating an immune response to a *Streptococcus*, or
(c) a fragment of (a) or (b) of at least 6 amino acids in length which is capable of generating an immune response against a *Streptococcus*.

In a further aspect, the invention relates to novel polynucleotides having a sequence which is:
(i) the nucleotide coding sequence of SEQ ID NO 1 or a sequence complementary thereto,
(ii) a nucleotide sequence which selectively hybridises to a said sequence (i) or fragment thereof, or
(iii) a nucleotide sequence which codes for a polypeptide having the same amino acid sequence as that encoded by a said sequence of (i) or (ii).

Polynucleotides are therefore provided which encode a polypeptide of the invention. The invention also provides:

a recombinant vector comprising a polynucleotide of the invention, such as an expression vector in which the polynucleotide is operably linked to a regulatory sequence;

a host cell which is transformed with a polynucleotide of the invention;

a process of producing a polypeptide of the invention comprising maintaining a host cell transformed with a polynucleotide of the invention under conditions to provide expression of the polypeptide;

an antibody, monoclonal or polyclonal, specific for a polypeptide as defined in claim 1; and a method of vaccinating a patient against a Streptococcal infection, which method comprises administering to the patient an effective amount of a polypeptide according to the invention.

DESCRIPTION OF THE SEQUENCES

Figure 1:
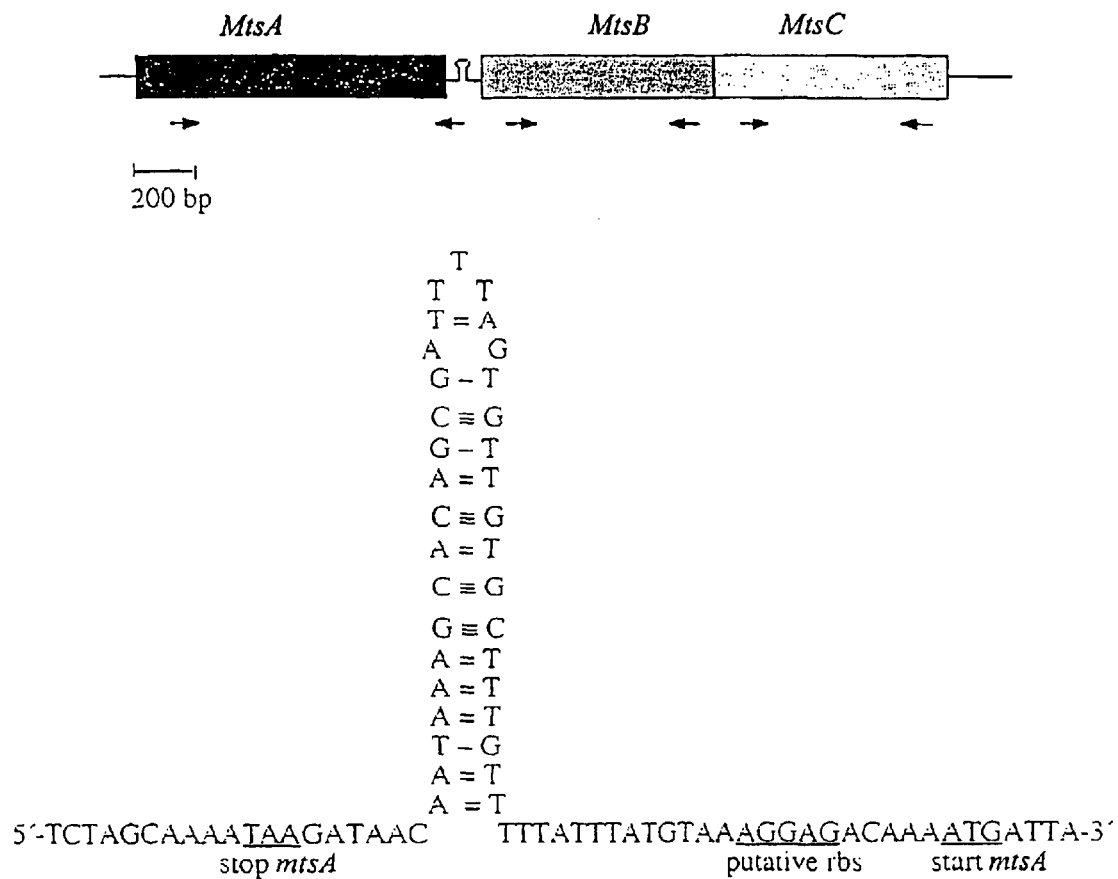
FIG. 1. Organization of the *S.pyogenes* lraI operon. The three genes in the *S.pyogenes* lraI operon are, from the left (5'), mtsA (lipoprotein), mtsB (ATP-binding protein), mtsC (integral membrane protein). Arrows indicate the location of primers used to verify the operon organization, and to create probes for each of the three genes. In the 66 bp non-coding region between mtsA and mtsB a putative stem-loop structure is present.

SEQ ID NO 1 sets out the amino acid sequence for the full length MtsA polypeptide of S.pyogenes and the nucleotide sequence encoding this protein. The structure of MtsA is discussed in more detail below.

SEQ ID NO 2 sets out the amino acid sequence for full length MtsA of S.pyogenes.

SEQ ID NO 3 and SEQ ID No 4 are examples of primers which may be used in the cloning of polynucleotides encoding MtsA.

SEQ ID NOs 5 to 9 are examples of MtsA peptides which may be used to generate anti-MtsA antisera.

DETAILED DESCRIPTION OF THE INVENTION

The invention provides a polypeptide consisting essentially of (a) the amino acid sequence of SEQ ID NO 1; (b) a variant of the amino acid sequence of SEQ ID NO 1; or (c) a fragment of at least 6 amino acids in length of (a) or (b). Typically the polypeptide is capable of binding an anti-MtsA antibody.

Antibody to MtsA can be raised against purified MtsA protein using protein purified directly from S.pyogenes expressing this protein as described in more detail below. Alternatively, protein can be generated recombinantly. Following purification of the protein, antibody can be raised in an animal such as a rabbit and purified to generate the desired antibody. The antibody can be monoclonal or polyclonal antibody. Preferably, the polypeptide of the invention is incorporated in a vaccine composition for immunisation against a Streptococcal infection. Preferably, the antibody is neutralising antibody. Preferably, a polypeptide of the invention generates anti-MtsA antibody when administered in vivo and provides protection against subsequent Streptococcal infection. Preferably, a polypeptide of the invention provides protection against group A Streptococcus but may also be used to provide vaccines against other Streptococcus such as S.pnuemoniae.

Polypeptides for incorporation into the vaccine compositions in accordance with the invention can be identified by determining whether they bind to an antibody specific for MtsA. Alternatively, antibody to a candidate polypeptide can be generated by standard techniques, for example by injection of the polypeptide into an appropriate animal and subsequent collection and purification of antisera from such animals. Antibody which binds MtsA can then be identified by standard and competitive immunoassays. The antibody thus identified can then be injected into mice to determine if it protects against a lethal challenge with a Streptococcal strain. Alternatively, an otherwise lethal dose of a strain of Streptococcus is given in an animal model system in which the animals have been given the relevant polypeptide.

As noted above a variant polypeptide (b) is one which will bind with an anti-MtsA antibody. Alternatively, a variant for incorporation into a vaccine composition is one which can be used to generate an immune response to provide protection against a Streptococcal infection. A variant of SEQ ID No 2 may be a naturally occurring variant which is expressed by another strain of S.pyogenes. Such variants may be identified by looking for a metal transporter protein in these strains which has a sequence which is highly conserved compared to SEQ ID No 2. Such proteins may be identified by analysis of the polynucleotide encoding such a protein isolated from alternative strains of S.pyogenes for example by carrying out the polymerase chain reaction using primers derived from portions of SEQ ID No 1. The Examples below demonstrate identification of MtsA derived from a number of S.pyogenes strains. Primers hybridizing to portions of the DNA sequence of SEQ ID No 1 such as those of SEQ ID No 3 or 4 can be used in the cloning and sequencing of MtsA from other S.pyogenes strains. MtsA antisera generated, for example, using the peptide of SEQ ID No 8 may be used to identify MtsA expressed by other S.pyogenes strains.

Variants of SEQ ID No 1 include sequences which vary from SEQ ID No 1 but are not necessarily naturally occurring MtsA. Over the entire length of the amino acid sequence of SEQ ID NO 1, a variant will preferably be at least 80% homologous to that sequence based on amino acid identity. More preferably, the polypeptide is at least 85% or 90% and more preferably at least 95%, 97% or 99% homologous to the amino acid sequence of SEQ ID NO 1 over the entire sequence. There may be at least 80%, for example at least 85%, 90% or 95%, amino acid identity over a stretch of 40 or more, for example 60, 100 or 120 or more, contiguous amino acids ("hard homology").

Amino acid substitutions may be made to the amino acid sequence of SEQ ID NO 1, for example from 1, 2 or 3 to 10, 20 or 30 substitutions. Conservative substitutions may be made, for example, according to the following table. Amino acids in the same block in the second column and preferably in the same line in the third column may be substituted for each other:

| ALIPHATIC | Non-polar | G A P |
|---|---|---|
| | | I L V |
| | Polar - uncharged | C S T M |
| | | N Q |
| | Polar - charged | D E |
| | | K R |
| AROMATIC | | H F W Y |

One or more amino acid residues of the amino acid sequence of SEQ ID NO 1 may alternatively or additionally be deleted. From 1, 2 or 3 to 10, 20 or 30 residues may be deleted, or more. Polypeptides of the invention also include fragments (c) of the above-mentioned sequences. Such fragments retain the ability to bind anti-MtsA antibody. Fragments may be at least from 10, 12, 15 or 20 to 60, 100 or 200 amino acids in length. Particularly preferred fragments comprise;

the sequence from amino acid residue number 136 through to residue 152 of SEQ ID NO 1, having the sequence KQLIAKDPKNKETYEKN (SEQ ID No 5);

the sequence commencing at position 204 through to 222 of SEQ ID NO 1, having the sequence EINTEEEGTPDQISSLIEK (SEQ ID No 6);

the sequence commencing at position 234 of SEQ ID NO 1 through to position 249 having the sequence ESSVDRRPMETVSKDS (SEQ ID No 7);

the sequence commencing at position 259 of SEQ ID NO 1 through to position 279, having the sequence TDSIAKKGKPGDSYYAMMKWN (SEQ ID No 8); and variants of these sequences.

One or more amino acids may be alternatively or additionally added to the polypeptides described above. An extension may be provided at the N-terminus or C-terminus of the amino acid sequence of SEQ ID NO 1 or polypeptide variant or fragment thereof. The or each extension may be quite short, for example from 1 to 10 amino acids in length. Alternatively, the extension may be longer. A carrier protein may be fused to an amino acid sequence according to the invention. A fusion protein incorporating the polypeptides described above can thus be provided.

Polypeptides of the invention may be in a substantially isolated form. It will be understood that the polypeptide may be mixed with carriers or diluents which will not interfere with the intended purpose of the polypeptide and still be regarded as substantially isolated. A polypeptide of the invention may also be in a substantially purified form, in which case it will generally comprise the polypeptide in a preparation in which more than 90%, e.g. 95%, 98% or 99%, by weight of the polypeptide in the preparation is a polypeptide of the invention.

Polypeptides of the invention may be modified for example by the addition of histidine residues to assist their identification or purification or by the addition of a signal sequence to promote their secretion from a cell where the polypeptide does not naturally contain such a sequence. It may be desirable to provide the polypeptides in a form suitable for attachment to a solid support. For example the polypeptides of the invention may be modified by the addition of a cysteine residue.

A polypeptide of the invention above may be labelled with a revealing label. The revealing label may be any suitable label which allows the polypeptide to be detected. Suitable labels include radioisotopes, e.g. $^{125}$I, $^{35}$S, enzymes, antibodies, polynucleotides and linkers such as biotin. Labelled polypeptides of the invention may be used in diagnostic procedures such as immunoassays in order to determine the amount of a polypeptide of the invention in a sample.

Polypeptides or labelled polypeptides of the invention may be used in serological or cell mediated immune assays for the detection of immune reactivity to said polypeptides in animals and humans. Standard protocols can be used. The labelled polypeptide may be used to identify and/or isolate "accessory" proteins which are involved in binding between cell receptors and MtsA, by detecting the interaction of MtsA to such proteins.

A polypeptide or labelled polypeptide of the invention or fragment thereof may also be fixed to a solid phase, for example the surface of an immunoassay well or dipstick.

Such labelled and/or immobilized polypeptides may be packaged into kits in a suitable container optionally including additional suitable reagents, controls or instructions and the like. The kits may be used to identify MtsA inhibitors or activators.

Such polypeptides and kits may also be used in methods of detection of antibodies to the MtsA protein by immunoassay.

Immunoassay methods are well known in the art and will generally comprise:
(a) providing a polypeptide comprising an epitope bindable by an antibody against said protein;
(b) incubating a biological sample with said polypeptide under conditions which allow for the formation of an antibody-antigen complex; and
(c) determining whether antibody-antigen complex comprising said polypeptide is formed.

The proteins of the present invention may be isolated from *S.pyogenes* expressing the protein. Proteins and peptides of the invention may be prepared as fragments of such isolated proteins. The proteins and peptides of the invention may also be made synthetically or by recombinant means. The amino acid sequence of proteins and polypeptides of the invention may be modified to include non-naturally occurring amino acids or to increase the stability of the compound. When the proteins or peptides are produced by synthetic means, such amino acids may be introduced during production. The proteins or peptides may also be modified following either synthetic or recombinant production.

The proteins or peptides of the invention may also be produced using D-amino acids. In such cases the amino acids will be linked in reverse sequence in the C to N orientation. This is conventional in the art for producing such proteins or peptides.

A number of side chain modifications are known in the art and may be made to the side chains of the proteins or peptides of the present invention. Such modifications include, for example, modifications of amino acids by reductive alkylation by reaction with an aldehyde followed by reduction with $NaBH_4$, amidination with methylacetimidate or acylation with acetic anhydride.

The polypeptides of the invention may be introduced into a cell by in situ expression of the polypeptide from a recombinant expression vector. The expression vector optionally carries an inducible promoter to control the expression of the polypeptide.

Such cell culture systems in which polypeptides of the invention are expressed may be used in assay systems.

A polypeptide of the invention can be produced in large scale following purification by high pressure liquid chromatography (HPLC) or other techniques after recombinant expression as described below.

A polynucleotide of the invention typically is a contiguous sequence of nucleotides which is capable of hybridising selectively with the coding sequence of SEQ ID NO 1 (nucleotides 1 to 861) or to the sequence complementary to that coding sequence. Polynucleotides of the invention include variants of the coding sequence of SEQ ID NO 1 which encode the amino acid sequence of SEQ ID NO 1 and variants and fragments of that sequence which are recognized by antibody to MtsA.

A polynucleotide of the invention and the coding sequence of SEQ ID NO 1 can hybridize at a level significantly above background. Background hybridization may occur, for example, because of other cDNAs present in a cDNA library. The signal level generated by the interaction between a polynucleotide of the invention and the coding sequence of SEQ ID NO 1 is typically at least 10 fold, preferably at least 100 fold, as intense as interactions between other polynucleotides and the coding sequence of SEQ ID NO 1. The intensity of interaction may be measured, for example, by radiolabelling the probe, e.g. with $^{32}$P. Selective hybridization is typically achieved using conditions of medium to high stringency (for example 0.03M sodium chloride and 0.03M sodium citrate at from about 50° C. to about 60° C.).

A nucleotide sequence capable of selectively hybridizing to the DNA coding sequence of SEQ ID NO 1 or to the sequence complementary to that coding sequence will be generally at least 80%, preferably at least 90% and more preferably at least 95%, homologous to the coding sequence of SEQ ID NO 1 or its complement over a region of at least 20, preferably at least 30, for instance at least 40, 60 or 100 or more contiguous nucleotides or, indeed, over the full length of the coding sequence. Thus there may be at least 85%, at least 90% or at least 95% nucleotide identity over such regions.

Any combination of the above mentioned degrees of homology and minimum size may be used to define polynucleotides of the invention, with the more stringent combinations (i.e. higher homology over longer lengths) being preferred. Thus for example a polynucleotide which is at least 85% homologous over 25, preferably over 30, nucleotides forms one aspect of the invention, as does a polynucleotide which is at least 90% homologous over 40 nucleotides.

For example the UWGCG Package provides the BESTFIT program which can be used to calculate homology (for example used on its default settings).

(Devereux etal (1984) *Nucleic Acids Research* 12, p387–395). The PILEUP and BLAST algorithms can be used to calculate homology or line up sequences (such as identifying equivalent or corresponding sequences (typically on their default settings), for example as described in Altschul S. F. (1993) J Mol Evol 36:290–300; Altschul, S, F et al (1990) J Mol Biol 215:403–10.

Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSP's containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Aced. Sci.* USA 89: 10915–10919) alignments by) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci.* USA 90: 5873–5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

Polynucleotides of the invention may comprise DNA or RNA. They may also be polynucleotides which include within them synthetic or modified nucleotides. A number of different types of modification to polynucleotides are known in the art. These include methylphosphate and phosphorothioate backbones, addition of acridine or polylysine chains at the 3' and/or 5' ends of the molecule. For the purposes of the present invention, it is to be understood that the polynucleotides described herein may be modified by any method available in the art.

Polynucleotides of the invention may be used to produce a primer, e.g a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein. SEQ ID Nos 3 and 4 are examples of primers of the invention.

Polynucleotides such as a DNA polynucleotide and primers according to the invention may be produced recombinantly, synthetically, or by any means available to those of skill in the art. They may also be cloned by standard techniques. The polynucleotides are typically provided in isolated and/or purified form, In general, primers will be produced by synthetic means, involving a step wise manufacture of the desired nucleic acid sequence one nucleotide at a time. Techniques for accomplishing this using automated techniques are readily available in the art.

Longer polynucleotides will generally be produced using recombinant means, for example using PCR (polymerase chain reaction) cloning techniques. This will involve making a pair of primers (e.g. of about 1530 nucleotides) to a region of the mtsA gene which it is desired to clone, bringing the primers into contact with DNA obtained from a bacterial cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Such techniques may be used to obtain all or part of the mtsA gene sequence described herein. Genomic clones containing the mtsA gene and its promoter region may also be obtained in an analogous manner, starting with genomic DNA from a bacterial cell.

Although in general the techniques mentioned herein are well known in the art, reference may be made in particular to Sambrook et al, 1989.

Polynucleotides or primers of the invention may carry a revealing label. Suitable labels include radioisotopes such as $^{32}P$ or $^{35}S$, enzyme labels, or other protein labels such as biotin. Such labels may be added to polynucleotides or primers of the invention and may be detected using techniques known per se.

Polynucleotides or primers of the invention or fragments thereof, labelled or unlabelled, may be used by a person skilled in the art in nucleic acid-based tests for detecting or sequencing MtsA in a sample.

Such tests for detecting generally comprise bringing a sample containing DNA or RNA into contact with a probe comprising a polynucleotide or primer of the invention under hybridizing conditions and detecting any duplex formed between the probe and nucleic acid in the sample. Such detection may be achieved using techniques such as PCR or by immobilizing the probe on a solid support, removing nucleic acid in the sample which is not hybridized to the probe, and then detecting nucleic acid which has hybridized to the probe. Alternatively, the sample nucleic acid may be immobilized on a solid support, and the amount of probe bound to such a support can be detected.

The probes of the invention may conveniently be packaged in the form of a test kit in a suitable container. In such kits the probe may be bound to a solid support where the assay formats for which the kit is designed requires such binding. The kit may also contain suitable reagents for treating the sample to be probed, hybridizing the probe to nucleic acid in the sample, control reagents, instructions, and the like.

Polynucleotides of the invention can be incorporated into a recombinant replicable vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells are described below in connection with expression vectors.

Preferably, a polynucleotide of the invention in a vector is operably linked to a control sequence which is capable of providing for the expression of the coding sequence by the host cell, i.e. the vector is an expression vector. Such expression vectors can be used to express the polypeptide of the invention.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences.

Such vectors may be transformed into a suitable host cell to provide for expression of a polypeptide of the invention. Thus, a polypeptide according to the invention can be obtained by cultivating a host cell transformed or transfected with an expression vector as described above under conditions to provide for expression of the polypeptide, and recovering the expressed polypeptide.

The vectors may be for example, plasmid, virus or phage vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid. Promoters and other expression regulation signals may be selected to be compatible with the host cell for which the expression vector is designed.

Host cells transformed (or transfected) with the polynucleotides or vectors for the replication and expression of polynucleotides of the invention will be chosen to be compatible with the said vector and preferably will be bacterial such as *E. coli*. Alternatively they may be cells of a human or animal cell line such as CHO or COS cells, or yeast or insect cells. The cells may also be cells of a non-human animal such as a sheep or rabbit or plant cells.

The polypeptides of the invention are useful for vaccinating against a Streptococcal infection, for example against group A *Streptococcus* or *S.pneumoniae*. A vaccine of the invention comprises a suitable polypeptide and a pharmaceutically acceptable carrier or diluent. The preparation of vaccines which contain an immunogenic polypeptide(s) as active ingredient(s), is known to one skilled in the art. Typically, such vaccines are prepared as injectables, either as liquid solutions or suspensions; solid forms suitable for solution in, or suspension in, liquid prior to injection may also be prepared. The preparation may also be emulsified, or the protein encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants which enhance the effectiveness of the vaccine.

Examples of adjuvants which may be effective include but are not limited to: aluminium hydroxide, N-acetyl-muramyl-L-threonyl-D-isoglutamnin (thr-MDP), N-acetyl-nor-muramyl-L-alanyl-D-isoglutamine (CGP 11637, referred to as nor-MDP), N-acetylmuramyl-L-alanyl-D-isoglutamnyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against an immunogenic polypeptide containing MtsA antigenic sequence resulting from administration of this polypeptide in vaccines which are also comprised of the various adjuvants.

The vaccines are conventionally administered parentally, by injection, for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, preferably 1% to 2%. Oral formulations include such normally employed excipients as, for example, pharmaceutical grades of mannitol, lactose, starch, magnesium stearate, sodium saccarine, cellulose, magnesium carbonate, and the like. These compositions take the form of solutions, suspensions, tablets, pills, capsules, sustained release formulations or powders and contain 10% to 95% of active ingredient, preferably 25% to 70%. Where the vaccine composition is lyophilised, the lyophilised material may be reconstituted prior to administration, e.g. as a suspension. Reconstitution is preferably effected in buffer.

Capsules, tablets and pills for oral administration to a patient may be provided with an enteric coating comprising, for example, Eudragit "S", Eudragit "L", cellulose acetate, cellulose acetate phthalate or hydroxypropylmethyl cellulose.

The polypeptides of the invention may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric and maleic. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine and procaine.

The vaccines are administrated in a manner compatible with the dosage formulation and in such amount as will be prophylactically effective. The quantity to be administered, which is generally in the range of 5 $\mu$g to 100 mg, preferably 250 μg to 10 mg, of polypeptide (antigen) per dose, depends on a number of factors. These include the subject to be treated, capacity of the subject's immune system to synthesize antibodies, and the degree of protection desired. Precise amounts of active ingredient required to be administered may depend on the judgement of the practitioner and may be peculiar to each subject.

The vaccine may be given in a singe dose schedule, or preferably in a multiple dose schedule. A multiple dose schedule is one in which a primary course of vaccination may be with 1–10 separate doses, followed by other doses given at subsequent time intervals required to maintain and or reinforce the immune response, for example at 1 to 4 months for a second dose, and if needed, a subsequent dose(s) after several months. The dosage regimen will also, at least in part, be determined by the need of the individual and be dependent upon the judgement of the practitioner.

The nucleotide sequences of the invention and expression vectors can also be used as vaccine formulations as outlined above. The vaccines may comprise naked nucleotide sequences or be in combination with cationic lipids, polymers or targeting systems. The vaccines may be delivered by any technique suitable for delivery of nucleic acid vaccines.

The immunogenic polypeptides prepared as described above can be used to produce antibodies, both polyclonal and monoclonal. If polyclonal antibodies are desired, a selected mammal (e.g., mouse, rabbit, goat, horse, etc.) is immunised with an immunogenic polypeptide of the invention. Serum from the immunised animal is collected and treated according to known procedures. If serum containing polyclonal antibodies to the polypeptide contains antibodies to other antigens, the polyclonal antibodies can be purified by immunoaffinity chromatography. Techniques for producing and processing polyclonal antisera are known in the art.

Monoclonal antibodies directed against Streptococcal epitopes in the polypeptides of the invention can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced against polypeptides of the invention can be screened for various properties; i.e., for isotype and epitope affinity. Preferably the antibody is specific for a MtsA protein epitope.

Antibodies, both monoclonal and polyclonal, which are directed against polypeptides of the invention are particularly useful in diagnosis, and those which are neutralising are useful in passive immunotherapy. Monoclonal antibodies, in particular, may be used to raise anti-idiotype antibodies. Anti-idiotype antibodies are immunoglobulins which carry an "internal image" of the antigen of the infectious agent against which protection is desired.

Techniques for raising anti-idiotype antibodies are known in the art. These anti-idiotype antibodies may also be useful for treatment of Streptococci, as well as for an elucidation of the immunogenic regions of polypeptides of the invention.

It is also possible to use fragments of the antibodies described above, for example, Fab fragments. Antibodies generated to a peptide of the invention may be administered to an individual to treat GAS infection by passive immuno therapy. The antibodies of the invention may be formulated with a pharmaceutically acceptable carrier and delivered in the same way as set out above for the vaccine compositions. Preferably the antibody is administered in an amount effective to ameliorate GAS infection in the individual.

The following Examples illustrate the invention.

EXAMPLES

Experimental Procedures Used in the Following Examples

Bacterial Cultures

The *S.pyogenes* strains used in this study (serotypes M1, M4, M9, M12, M49) are from the World Health Organization Centre for references and research on *Streptococci*, Institute of Hygiene and Epidemiology, Prague, Czech Republic. The *S.pyogenes* strain SF370 is being sequenced in the Streptococcal Genome Project, and can be obtained from ATCC (700294). *Streptococci* were grown in Todd-Hewitt broth (Difco, Detroit, Mich.), supplemented with 0.2% yeast extract (Difco) in 5% $CO_2$ at 37° C. *E. coli* strain BL21 (Pharmacia Biotech, Uppsala, Sweden) was grown in Luria-Bertani or 2X YT broth or agar, aerobically at 37° C. and supplemented with 100 μg/ml ampicillin (Sigma, St Louis, Mo.) or glucose where appropriate.

PCR, Cloning Procedures, and Sequencing

Chromosomal DNA from *S.pyogenes* strains was extracted as described in Pitcher et al, Lett. App. Microbiol 1989 8 p151–156 modified in the initial incubation step by addition of 1000 U/ml of mutanolysin (Sigma) and 100 mg/ml lysozyme (Sigma). Oligonucleotide primers were designed by using sequence information from the Streptococcal Genome Project database, together with published sequences from other *Streptococcus* spp. Primers 5'-TAG-TAG-CGA-ATT-CGT-CGA-CTG-GCG-CTA-3' (SEQ ID NO 3) and 5'-AGC-ACA-ACT-CGA-GAA-TCG-CTG-TGC-TTT-A-3' (SEQ ID NO 4) enclose almost the whole of mtsA (excluding the signal peptide and the $NH_2$-terminal cysteine residue) and were designed with an EcoRI and XhoI restriction site, respectively. Primers 5'-GAT-TAC-AAC-TAA-CAA-TCT-TTG-TGT-GAC-C-3' (SEQ ID NO 10), 5'-TTG-ACA-AGG-TAT-CAA-CAG-TAA-ATA-CCT-C-3' (SEQ ID NO 11). 5'-ATG-TCA/T-CTC/T-ATG-GGA/ G/T-GAT-GCC-ATC-3' (SEQ ID NO 12), and 5'-TTA/G-GCA-TAT/G-AG/AA-TAA/G-GCC/T-GTC-GC-3' (SEQ ID NO 13) were designed from internal segments of the genes mtsB and mtsC. PCR experiments were performed using Taq polymerase (Gibco-BRL, Gaithersburg, Md.), except for cloning purposes, when TaqPlus Precision™ (Strategene, La Jolla, Calif.) was used. The PCR product corresponding to mtsA was gel-purified prior to cloning, using Sephaglas™ Bandprep Kit (Pharmacia Biotech). The PCR profile consisted of 30 cycles at 94° C. for 1 min, 50° C. for 1 min, and 72° C. for 2 min, followed by a final extension at 72° C. for 7 min. Plasmid purification, restriction enzyme digestions, ligation, electroporation and screening of transformants were all performed according to standard procedures, or when applicable, according to instructions in the GST fusion protein kit (Pharmacia). Sequencing of the cloned insert was performed on an ABI-470 Prism with dyed dideoxy terminators, at Innovagen AB, Lund, Sweden.

Overexpression and Purification of Recombinant MtsA

An *E. coli* strain carrying the recombinant plasmid pGEX-5X-3:mtsA was grown at 37° C. overnight. This preculture was then inoculated 1:100 in prewarmed 2×YT containing 100 μg/ml ampicillin. The culture was grown at 30° C. until $OD_{600}$=1.2. Induction was then started by adding 0.5 mM IPTG (Promega, Madison, Wis. After an additional 4 h of incubation the bacteria were pelleted by centrifugation at 8000×g for 10 min, washed, and resuspended in PBS buffer, and lysed by sonication with a Branson sonifier B15 (Heimstatt, Germany). Triton X-100 was added to a final concentration of 10/, and the sample was gently mixed for 30 min. Cell debris was pelleted by centrifugation at 12000×g for 10 min, and the supernatant was applied to a pre-equilibrated glutathione-sepharose suspension. All washes were performed in batch format, by centrifugation at 1000×g for 5 min. GST:MtsA fusion protein was eluted with reduced glutathione. Alternatively, factor Xa cleavage (Pharmacia Biotech) was performed in 50 mM Tris-HCl, pH 7.5, 150 mM NaCl, 1 mM CaCl$_2$, overnight (1 U factor Xa/ml bacterial sonicate supernatant). Cleaved MtsA protein was then eluted in repeated steps with PBS.

RNA methods

Total RNA from *S.pyogenes* was purified using Fastprep™ cell disrupter (Savant, Holbrook, N.Y.). Briefly, bacteria were cultured in THY medium until mid-logarithmic or early stationary phase, harvested by centrifugation at 3,800×g for 10 min at 4° C., and resuspended in PBS, followed by disruption for 2×30 seconds at setting 6.0 using FastRNA™ kit with glass beads (BIO 101, Vista, Calif.) according to the manufacturers instructions.

For Northern blot experiments, RNA was separated on 1% agarose in 1×HEPES buffer, blotted onto Hybond-N filters (Amersham, Amersham, UK), and hybridized with 600–900 bp long DNA probes specific for mtsA, mtsB and mtsC (see above). The PCR products (see above) were purified on a MicroSpin™ S-200 HR column (Pharmacia, Uppsala, Sweden), and radiolabelled with [α-$^{32}$P]dATP using the Megaprime™ kit (Amersham). To verify that equal amounts of RNA were present on the filter, it was also probed with a radiolabelled 800 bp probe specific for 16S rRNA.

Protein Methods

Protein samples were separated by 12% SDS-PAGE. Gels were then soaked in blotting buffer (20% ethanol, 200 mM glycine, 25 mM Tris), and proteins were blotted to an Immunobilon-P™ PVDF-membrane (Millipore). Membranes were then blocked in 15 ml of PBS, 0.05% Tween-20, 5% (w/v) skim milk for 20 min at room temperature. The primary antibody (see below) was added, diluted 1:1000 in PBS, 0.05% Tween-20 (PBST), and the membrane was incubated at 37° C. for 30 mins. Membranes were then washed in PBST, 3×5 min at 37° C. Horseradish peroxidase-conjugated antirabbit goat antibodies (Bio-Rad, Bio-Rad laboratories CA) diluted 1:3000 in PBST were added and the membrane was incubated for 30 min at 37° C., and then washed as above.

Proteolytic digestion of bacteria was performed on overnight cultures of *S. pyogenes*. Bacteria were pelleted by centrifugation at 3000×g for 5 min, at 8° C., resuspended in cleavage buffer (0.01 M Tris-HCl, pH 8), and washed twice as above before being resuspended in cleavage buffer. Papain (Sigma) was added (0–200 µg/2×10$^9$ bacteria), and digestion was initiated by the addition of L-cysteine (55 mM). The suspension was incubated at 37° C. for 1 h. The digestion was stopped by adding Iodoacetamide to a final concentration of 12 µM. Bacteria were then pelleted by centrifugation at 4800×g for 10 min, and the supernatant was removed and filtered through a 0.2 µm Acrodisc (Gelman Sciences, Ann Arbor, Mich.). After freezing and thawing, samples precipitated spontaneously. This was used as a convenient method of concentration, as SDS-PAGE analysis indicated that the precipitate contained all the proteins present in the original solubilized sample. Enzymatic digestion with streptococcal cysteine proteinase was performed essentially as described in Berge and Björck, J. Biol Chem (1995) 270 9862–9867.

Metal Assays

Samples for PIXE analysis were prepared as follows. One ml of GST, MtsA fusion, and MtsA suspended in PBS was ultrafiltrated in Centricon-10 cells (Amicon, Inc., Beverly, Mass.) four times, each time reducing the volume to less than one tenth, and adding Millipore water up to 1.5 ml after the first three spins. The final protein concentration was determined using Coomassie® Protein Assay Reagent kit (Pierce, Rockford, Ill.). Bovine iron-saturated holo-Transferrin (Sigma) was suspended in Millipore water. Then, 20 and 60 µg of GST, MtsA fusion and MtsA, respectively, in 25 ll of Millipore water was added to a Kimfoil (Kimberley Clark), mounted on a plastic frame, and allowed to dry. 200 µg of transferrin in 25 µl of Millipore water was similarly prepared. At the Lund Nuclear Microprobe the samples were placed in the vacuum irradiation chamber and bombarded with a 2 nA proton beam, having an energy 2.55 MeV, accumulating a beam charge of 0.6 µC. The characteristic X-rays emitted were detected using a Kevex 50 mm$^2$ Si(Li) X-ray detector, while data were collected using a CAMAC/Mac-computer system equipped with KMAX (Sparrow) software. Elemental standards (Fe, Co, Ni) were analysed in the same batch to verify quantification.

Gel filtration experiments were performed with PD-10 columns (Pharmacia Biotech). 20 µg protein (GST or MtsA) in PBS, supplemented with 0.25 M NaCl, was incubated overnight at 4° C. with approx. 0.5 µCi of $^{54}$Mn, $^{65}$Zn or $^{59}$Fe (Amersham). The sample was applied to a gel filtration column, preequilibrated with PBS, 0.25 M NaCl, and 0.3 ml fractions were eluted with the same buffer. Each fraction was then assayed for protein content, using Coomassie® Protein Assay Reagent kit (Pierce), and radioactivity, by adding Ready Safe™ scintillation fluid (Beckman Instruments, Fullerton, Calif.) and counting Remission on a Beckman Instruments LS6000TA.

Slot blot experiments were performed by applying 10, 1 and 0.1 µg of protein (MtsA fusion and GST) to a nitrocellulose membrane, using a slot blot apparatus (Millipore). Membranes were equilibrated in 0.1 M citrate buffer, pH 6.2, (appr. 0.1 M Na$^+$), or 0.1 M maleic acid, pH 6.5, 0.1 M NaCl (for iron-binding) and then suspended in the same buffer with 1 µCi/ml of radioisotope ($^{59}$Fe, $^{54}$Mn or $^{65}$Zn), for 1 h at room temperature and with gentle mixing. In competition experiments 1 mM of Fe(II) sulfate, Fe(II) citrate, MnCl$_2$, CuCl$_2$ or ZnCl$_2$ was added. Then, membranes were washed for 2×15 min in buffer, and exposed on a phosphoimaging plate (Fuji Photo Film Co. Ltd., Japan). Quantification of bound radioactivity was performed using the Bio-Imaging Analyzer BAS2000 program package (Fuji Photo Film).

Other Methods

NH$_2$-terminal sequencing (Edman degradation) was performed at the Biomedical Service Unit, Lund University. The peptide QDPHEYEPLPEDV SEQ ID No 9 was synthesized, analysed for purity and correct sequence.

Rabbits were immunized with peptide-KLH conjugates. Primary immunization was performed with 100 µg peptide-KLH conjugate in Freunds complete adjuvant (Sigma). The two booster immunizations were done at weeks 4 and 6, using 100 µg peptide-KLH conjugate in Freunds incomplete adjuvant (Sigma).

Example 1

Identification and Sequence Analysis of a *S. pyogenes* Member of the lraI Family Predicted amino acid sequences of the proteins encoded by the various lraI operons were used to search (tBLASTn)

the Streptococcal Genome Project database, at the time of 95% completion. The products of four adjacent open reading frames (ORF), showed strong homology to the LraI proteins. A frame shift split one gene (lipoprotein) in two ORF's but subsequent sequencing (see below) of a serotype M1 strain showed that the database sequence was incorrect, containing a single base insertion in a region of reduced database sequence quality. The (corrected) three ORFs were named mtsABC (streptococcal metal transporter).

The three ORFs encode proteins typical of an ABC transport system. MtsA contains a putative hydrophobic signal peptide and a consensus sequence (LXXC) typical of $NH_2$-terminal lipid linkage bacterial lipoproteins. MtsB has an ATP-binding cassette, while MtsC is a highly hydrophobic protein with 67 potential transmembrane domains. Homologies between the putative proteins of S. pyogenes and their counterparts in other Streptococcus spp. were in the same range as previously described for the lraI family, as noted in the Table below. The percentages indicate sequence identity at the protein level. An "*" indicates only partial sequences available.

| Bacterium | Lipoprotein | ATP-binding protein | Integral membrane protein |
| --- | --- | --- | --- |
| S. pneumoniae | 72% | 51%* | 70% |
| S. gordonii | 73% | 56% | 78% |
| S. parasanguis | 72% | 54% | 75% |
| S. sanguis | 74% |  | 75%* |
| S. crista | 72% |  | 73%* |
| E. faecalis | 55% |  |  |

Notably, the arrangement of the genes in the S. pyogenes operon was atypical. The lipoprotein gene is at the 5'-end of the operon, whereas in all other operons it is at the 3' end. A publication on an oligopeptide permease ABC-transporter in S. pyogenes Polbielski et al Mol. Microbiol. 1996 21(5) 1087–1099 showed a differential transcription of the lipoprotein component. A putative stem-loop structure (−60.2 kJ $mol^{-1}$) (FIG. 1B) similar to Rho-independent transcription terminators was identified in the 66 bp non-coding region between MtsA and MtsBC.

The atypical organization was verified by PCR experiments. Forward and reverse primer pairs from each of the three genes were used to amplify products with template DNA from five different strains (serotypes M1, M4, M9, M12, and M49) of S. pyogenes, in combinations so as to allow every possible arrangement of the three genes in the operon. All experiments gave single products of a size consistent only with the atypical operon seen in the database (data not shown).

The GENBANK database was searched for homologues of MtsA, MtsB and MtsC, using the BLAST algorithm. The highest scoring matches were all ABC transporters specific for di-or trivalent cations. Specifically, several iron-siderophore transport systems showed a high degree of homology to the streptococcal proteins. MtsA has a 34% identify with YfeA (Bearden et al J. Bacteriol 1998 180(5) 1135–1147), the periplasmic binding protein of an iron (chelated) transport system in Yersinia pestis (also in Haemophilus influenzae). An inversely directed search, using YfeA to search for homologues in the Streptococcal Genome database, identified MtsA as the best homologue on the streprococcal genome. TroA (Hardman et al Gene 1997 197 47–64) from Treponema pallidum also shows homology (27% id. and 17% sim.) with MtsA, and is part of an ABC transporter operon flanked by iron-regulated transcription factors. Additionally, a recently described iron-regulated ABC transporter in Staphylococcus epidermidis (Cockayne et al Infect Immun 1998 66 3767–3774) has a high degree of homology (the S. epidermidis lipoprotein is 52% identical to MtsA) to lraI protein, and should possibly be included in this family.

Two homologous ABC transporters not involving iron were also found:

the manganese transporter MntABC (Bartsevich and Pakrasi EMBO J. 1995 14(9) 1845–1853) from Synechococcus cystis, and the zinc transporter AdcCBA from S. pneumoniae, where MtsA showed appr. 30% identity with the corresponding proteins, MntC and AdcA. A comparison of MtsC with conserved motifs of integral membrane proteins from ABC transporters (Saurin et al Mol Microbiol 1994 12 993–1004) showed that the best fitting (21% id. and 21% sim. on 43 aa) motif was from the cluster of iron-siderophore transporters.

Example 2

Transcriptional Analysis of mtsABC

In order to investigate the transcription of the three genes in the S. pyogenes lraI operon, probes corresponding to internal sequences of mtsA, mtsB and mtsC were produced and labelled. Total RNA was extracted from serotype M1 S. pyogenes bacteria grown to mid-logarithmic and early stationary phase. Northern blot experiments (data not shown) showed that all three probes reacted weakly with a transcript approximately 2.5 kb in size when RNA from mid-log phase bacteria was used, consistent with a polycistronic transcription of the operon. However, the mtsA probe also reacted with a shorter transcript, approximately 1 kb in size. This shorter transcript was present in higher (10–20 times) amounts than the polycistronic transcript, suggesting that the stem-loop structure in the non-coding region between mtsA and mtsB can terminate transcription. The MtsA probe showed weak reactivity with the short transcript when RNA from bacteria in early stationary phase was used, whereas the two other probes did not hybridize at all. A control hybridization with a probe for 16S rRNA was done to verify that RNA levels in the samples (mid-log and early stationary phase of growth) were equal (data not shown). Taken together, these results indicate that the lipoprotein is expressed in higher quantities than the ATPase and hydrophobic membrane protein.

Example 3

Surface Localization of the MtsA Lipoprotein

We produced the synthetic peptide QDPHEYEPLPEDV (SEQ ID NO 9), spanning a highly conserved region of MtsA, predicted to have good antigenicity. A rabbit was immunized with the peptide, and following three boosters the serum showed good reactivity with the peptide in ELISA, as compared with preimmune serum (data not shown). Then, a proteolytic digestion of S. pyogenes bacteria was performed, to investigate whether a protein fragment from the lipoprotein could be identified using the peptide antiserum. The protein fragments released by proteolytic digestion were subjected to SDS-PAGE and then transferred to PVDF-membrane by Western blotting.

Immunodetection with the peptide antiserum identified a protein fragment with an apparent molecular mass of 36 kDa, solubilized at high concentrations of papain (data not shown). The protein seemed fairly resistant to proteolytic digestion, since it remained at the same position even at high papain concentrations when most of the proteins had shifted to the low molecular weight range, supposedly degraded by the excess of protease. Protein from the 36 kDa band was subjected to $NH_2$-terminal amino acid sequencing. The result (KSDKLKVVAT (SEQ ID NO 14), aa 1–10 of the 36 kDa papain fragment) showed a 90% identity to a region very close to the $NH_2$-terminus in the predicted MtsA protein (amino acids 30–39) of the database (ESDKLKVVAT (SEQ ID NO 15), and a 100% identity to the predicted MtsA protein (amino acids 30–39) from the sequence of the strain studied (see below). The predicted molecular mass of the mature MtsA polypeptide was 32 kDa. Thus, papain seems to cleave MtsA very close to the protein's predicted $NH_2$-terminal lipid anchor, liberating almost the whole polypeptide from the bacterial cell surface. A similar papain digestion and western blot was also performed with the strain SF370 sequenced in the Streptococcal Genome Project, with the same result.

Bacterial growth media from overnight cultures of *S. pyogenes* was also examined for presence of MtsA, since bacterial lipoproteins are sometimes found in medium as well. No reactivity with the peptide antiserum was seen in TCA-precipitated proteins from medium. Also, mild detergent treatment of bacteria failed to solubilize any protein reacting with the antiserum.

*S. pyogenes* produces and secretes a cysteine proteinase, SCP. This protease has previously been shown to release functionally active fragments of streptococcal surface proteins. We performed proteolytic digestions of *S. pyogenes* with purified SCP. Solubilized proteins were visualized by SDS-PAGE and analysed by immunoblotting. There was no reactivity with the antiserum. To exclude that MtsA had been completely degraded, a double digestion was performed, first with SCP and then with papain. The amount of MtsA released, as judged by staining and immunoblotting, was unaffected by pretreatment with SCP (data not shown).

Example 4

Cloning and Purification of Recombinant MtsA

The mtsA gene from strain AP1 was PCR-amplified and cloned into pGEX and sequence analysis confirmed the presence of MtsA, showing 98% (amino acid) identity with the database sequence, well in line with what could be expected from two different strains of the same serotype (compare psaA from *S. pneumoniae* Berry and Paton Infect. Immun. 1996 64(12) 5255–5262. There was no frame shift in the sequenced ORF, indicating that the preliminary database sequence indeed contained an incorrect base insertion (see above). Also, the supposed error is found in a region where the database sequence is less accurate. MtsA was purified by affinity chromatography of over expressed MtsA fusion and subsequent proteolytic cleavage with factor Xa. The purified MtsA had an apparent molecular mass of 36 kDa, and comprised>95% of the protein content in the sample (data not shown).

Computer predictions (Robson-Garnier and Chou-Fasman algorithms) of MtsA secondary structure suggest a predominantly α-helical structure (45–60% of the protein). CD-spectroscopy of MtsA confirmed these predictions (data not shown).

Example 5

Analysis of Trace Element Content and Metal Binding Properties MtsA

Figure 2:
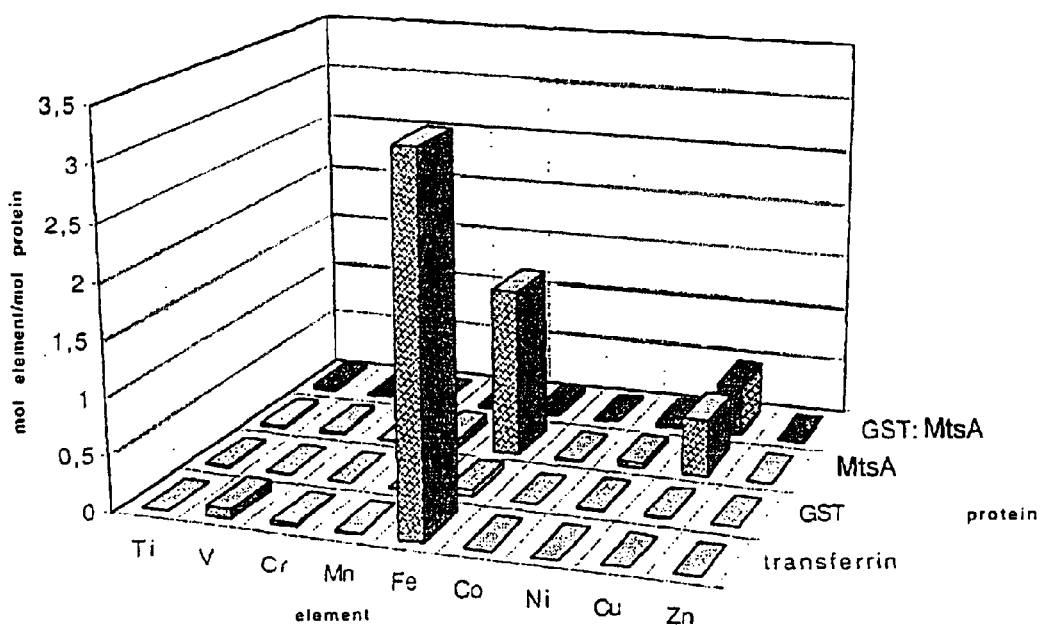
FIG. 2. Proton-induced X-ray emission analysis (PIXE). PIXE analysis of GST, GST:MtsA, MtsA and (iron-saturated) transferrin in millipore water. Results are based on two different experiments and shown in mol element per mol protein.

A recent publication on a periplasmic molybdate-binding protein of *E. coli* Rech et al J. Biol Chem 1996 271 2557–2562 showed that binding of the ligand changed the migration of the protein in native PAGE. Similar experiments were performed with MtsA, but no consistent effects on migration properties was seen with any of the tested potential ligands (Mn(II), Fe(III), Cu(II), Zn(II), Co(II), Ca(II)), nor with EDTA (data not shown). We performed a quantitative analysis of trace element content in MtsA, MtsA fusion, GST and (iron-saturated) transferrin by the use of a highly specific and sensitive technique, proton-induced X-ray emission (PIXE). PIXE analysis indicated that iron was present in approximately 1.5 molar ratio compared to protein in the MtsA sample (FIG. 2). Little or no iron was detected in the other samples, except for transferrin. Among other trace elements only copper was present in significant amounts. Both MtsA fusion and MtsA contained copper in approximately 0.5 molar ratio to protein. In a similar analysis, using a 0.1 M Tris-Ac buffer, pH 7.5, a significant Zn content was found (data not shown).

In addition, 30 μM solutions of GST and MtsA were analysed for iron content at a routine clinical chemistry laboratory. The sample with MtsA contained 20 μM iron, indicating a 67% saturation of the protein. To rule out that iron contamination from the factor Xa solution used for cleaving the fusion protein was affecting the results, a sample containing cleavage solution, reduced glutathione, and PBS was analysed for iron content. Iron concentration in chat sample was <5 μM (detection limit).

MtsA was subjected to proteolytic digestion with trypsin, papain, and proteinase K (5:1 ratio SmtA/protease). Digestion patterns of MtsA with/without pretreatment with EDTA were compared, to elucidate whether a potentially present cation ligand affected the conformation of the protein so as to change accessibility of proteolytic cleavage sites. No such effect was seen (data not shown). A relative resistance to proteolytic digestion with papain was noted, in accordance with the case of the native protein (see above). In addition a high degree of trypsin resistance was noted.

Figure 3:
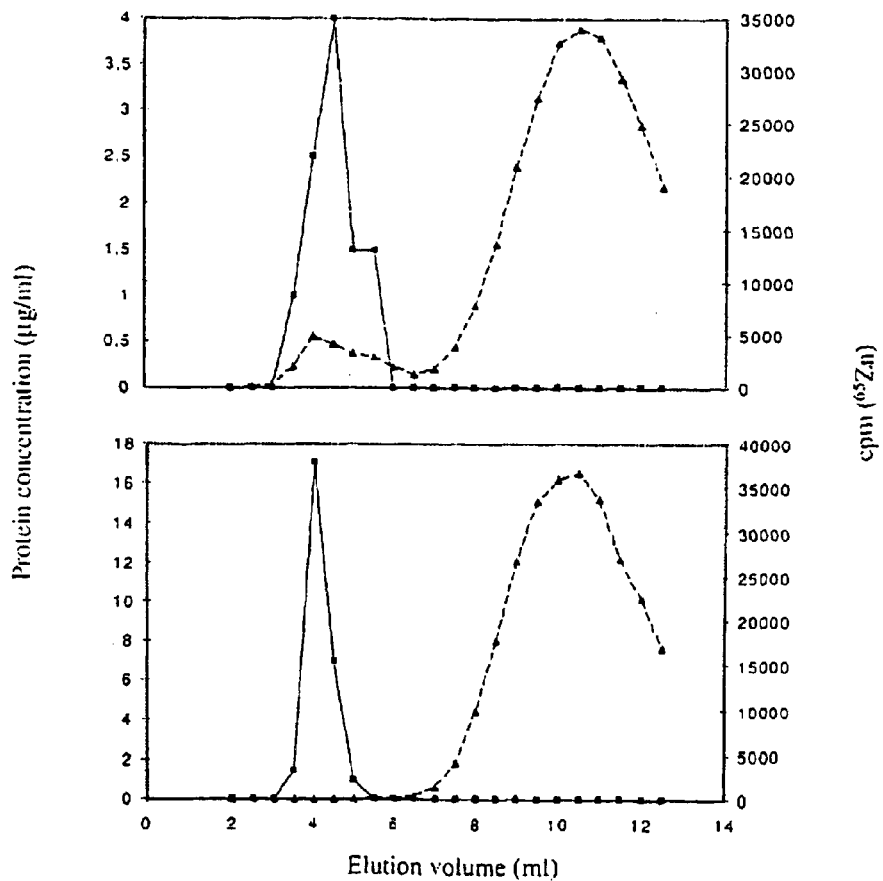
FIG. 3. Binding of $^{65}Zn$ to MtsA. A. MtsA and GST were separately incubated with $^{65}Zn$. The mixtures were subjected to gel filtration on a PD-10 column and 500 µl fractions were collected. Fractions were assayed for protein content and radioactivity. Co-migration of $^{65}$Zn and protein was seen in the MtsA sample (top graph) but not in the GST samples (bottom graph).

We chose to investigate direct binding of metal radioisotopes ($^{59}$Fe, $^{65}$Zn and $^{54}$Mn) to the recombinant protein. Iron proved to be notoriously difficult to work with, since ferric iron is essentially insoluble at neutral pH. Precipitation problems therefore prevented reasonable interpretation of several assays tried. Copper radioisotopes decay too rapidly to handle practically. Interestingly, an interaction with Zn could be demonstrated. GST and MtsA were incubated with $^{65}$Zn, in the presence of 0.25 M NaCl, and then subjected to gel filtration. Fractions were collected, and their protein concentration and radioactivity was measured. The result (FIG. 3A) indicates comigration of $^{65}$Zn with MtsA, but not with GST. When the molar amount of comigrating $^{65}$Zn is compared with the protein content, a 60% saturation of the protein is found (assuming a single binding site). Similarly incubated GST and MtsA were subjected to native PAGE, and then autoradiography. Radioactivity was seen at the place of MtsA, but not for GST (data not shown), and this could be inhibited by adding $ZnCl_2$ to the initial incubation.

A slot blot assay was also performed, applying MtsA and GST onto a nitrocellulose membrane in dilution series. The membrane was then incubated with $^{65}$Zn, and, following washing steps, radioactivity was found in the MtsA fusion sample, but not in the GST sample (data not shown). This interaction could be efficiently inhibited (88%) by addition of 1 mM $ZnCl_2$ during incubation. A varying degree of inhibition was seen when adding other metal salts. Among these, only Cu(II) inhibited the interaction to a high degree (74%). A similar experiment was performed with $^{59}$Fe(III), which also bound to MtsA but not to GST (data not shown).

The binding was completely inhibited by addition of 1 mM Fe(III) citrate, but only weakly inhibited by 1 mM $CuCl_2$ and $MnCl_2$. Addition of Fe(II)-sulfate or $ZnCl_2$ caused unspecific interaction with the membrane, probably due to precipitation. All these assays were also performed with $^{54}Mn$, but no interaction between the radioisotope and any of the proteins was found.

Example 6

Gene and Proton Prevalence

Genomic DNA was isolated and subjected to PCR, using the primers as listed, and an annealling temperature of 45 degrees. The primers used for PCR amplification of MtsA gene included:

LUND MTSA 5'-TAG-TAG-CGA-ATT-CGT-CGA-CTG-GCG-CTA-3'

(SEQ ID No 3)

MTSA 4 5'-AGC-ACA-ACT-CGA-GAA-TCG-CTG-TGC-TTT-A-3'

(SEQ ID No 4)

The PCR reagents and reagent volumes used for each sample were as follows: 10 μl GeneAmp 10×PCR Buffer II & $MgCl_2$, 5 μl LUND MTSA primer 10 μM, 5 μl MTSA 4 primer 10 μM, 10 μl DNTP mixture 2.5 mM (dATP, dCTP, dGTP, dTTP), 67.5 μl $dH_2O$, 2 μl Bacterial DNA template, 0.5 μl AmpliTaq Gold DNA polymerase. The thermocycler PCR settings were as follows: A. 94° C. for 10 minutes, B. 95° C. for 1 minute, C. 45° C. for 1 minute, D. 74° C. for 1 minute, E. 74° C. for 7 minutes, F. 0° C. tubes stored indefinitely. Steps B–D were cycled 35 times. All 23 strains have detectable PCR product in the predicted size range. The results are set out in Table 1 below.

Sequence Conservation

The MtsA PCR products from three strains of GAS have been sequenced, resulting in approximately 750 bp from each. The sequences showed a high level of conservation, compared to the sequence of the original AP1 strain. The strains sequenced were M1 AP1, T11 AP74 and M1 3686–98. The sequencing primers were identical to those used for the PCR, reaction.

Example 7

Generation of Antiserum

From the genbank MtsA sequence, a number of peptides have been selected based on predicted antigenicity. These are as follows:

QDP13    QDPHEYEPLPEDV (SEQ ID NO 9)    13

The first four peptides have been conjuguated to KLH and used to immunize two sheep each as follows: the peptides were derived from peptide synthesis by Genosys Biotechnologies Inc. They are supplied as conjugated lyophilized powder in 0.5 mg aliquots in capped vials. The peptides were conjugated to keyhole limpet hemocyanin. C* is a cysteine insert for attachment to a hetero bifunctional linker.

In addition, there were BSA-conjugates of the peptides. They were stored as lyophilized powder in 0.5 mg aliquots in capped vials. The BSA-conjugates were used for ELISA plate immobldization/evaluation.

For each immunisation the following regent mixture was administered:

A fixed volume of 3.25 ml Freund's complete/incomplete adjuvant.

1 mg of peptide conjugate in 1.3 ml volume of saline for the primary immunisation at day 0 or 0.5 mg of peptide conjugate in 1.3 ml volume of saline for the subsequent immunisations. The immunisation mixture was achieved by emulsifying the peptide-conjugates in saline with the Freund's adjuvant. The immunisation mixture was injected into 6 subcutaneous sites for each sheep.

These antisera have been tested by ELISA for their ability to bind to the immunizing peptides. Peptide was coated onto microtitre plates (100 μl/well) at a concentration of 5 μg/ml, in 0.05M carbonate-bicarbonate buffer pH 9.6. The plates were incubated for 1 hour at 37° C. The plates were then washed ×5 with PBS-T (250 μl/well) and blocked with 1% BSA/PBS-T (100 μl/well) for 1 hour at 37° C.

After washing the plates ×3 with PBST, pre and post immune sera from sheep immunised with peptide conjugate vaccine candidates including FCA/Spy LP-TDS21-KLH, FCA/Spy-LP-ESS16KLH, FCA/Spy-LP-KQL17-KLH and FCA/Spy-LP-EIN19-KLH were diluted 1/10,000 with PBS-T. The sera were then incubated on plates coated with the corresponding peptide (100 μl sera/well) for 1 hour, at 37° C. The plates were washed ×3 with PBST and incubated with donkey anti-sheep IgG/peroxidase conjugate (1/1000 in PBS-T) for 1 hour at 37° C. Aft er washing ×5 with PBS-T, the plates were incubated with 0.1 mg/ml TMB substrate (100 μl/well) for 10 minutes and then the reaction was stopped with 2M $H_2SO_4$ (50 μl/well). Absorbances were read at 450 nm.

Figure 4:
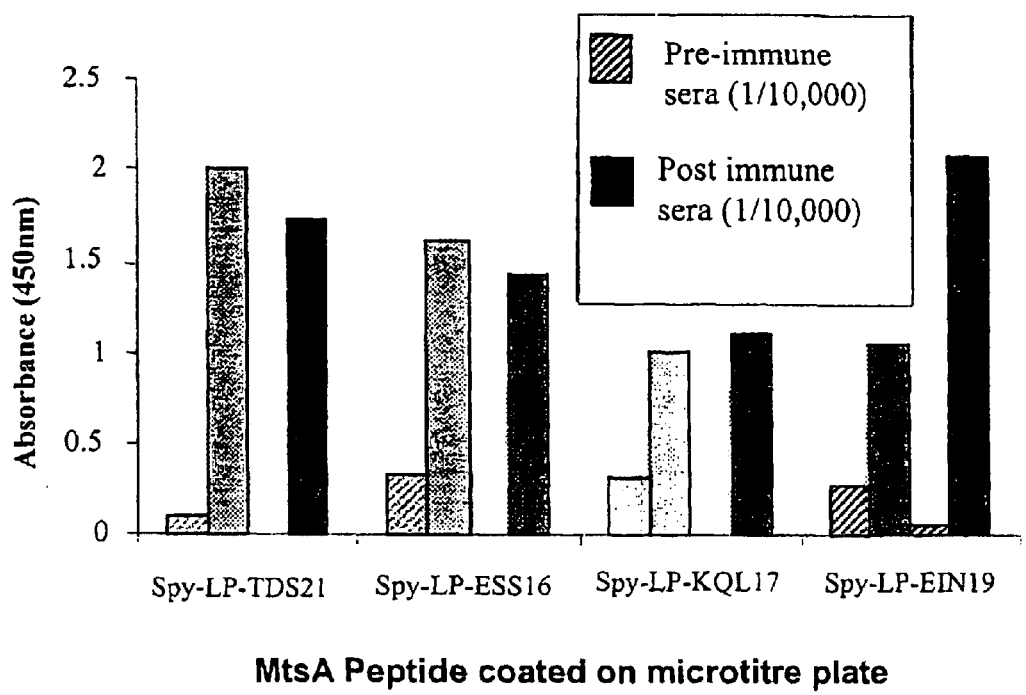
FIG. 4. Plots the results of sheep anti-MtsA antisera ELISA against plates coated with MtsA peptides.

FIG. 4 shows that both sheep immunized with each peptide raised strong antisera against the corresponding

| Name | Sequence (including terminal C) | | length |
|---|---|---|---|
| Spy-LP-TDS21 (259–280) | C*TDSIAKKGKP GDSYYAMMKW N-COOH | (SEQ ID NO 8) | 22 |
| Spy-LP-ESS16 (234–250) | C*ESSVDRRPME TVSKDS-COOH | (SEQ ID NO 7) | 17 |
| Spy-LP-KQL17 (136–153) | C*KQLIAKDPKN KETYEKN-COOH | (SEQ ID NO 5) | 18 |
| Spy-LP-EIN19 (204–223) | C*EINTEEEGTP DQISSLIEK-COOH | (SEQ ID NO 6) | 20 |

Figure 5:
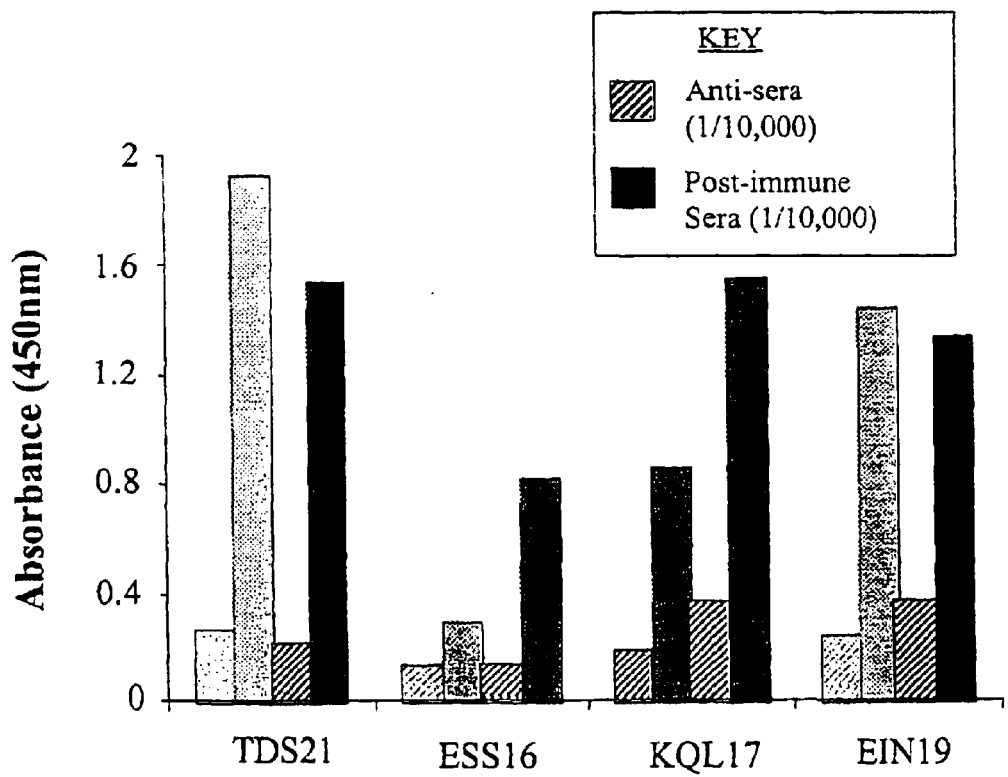
FIG. 5. Plots the results of sheep anti-MtsA peptide antisera ELISA against plates coated with MtsA protein.
Figure 6:
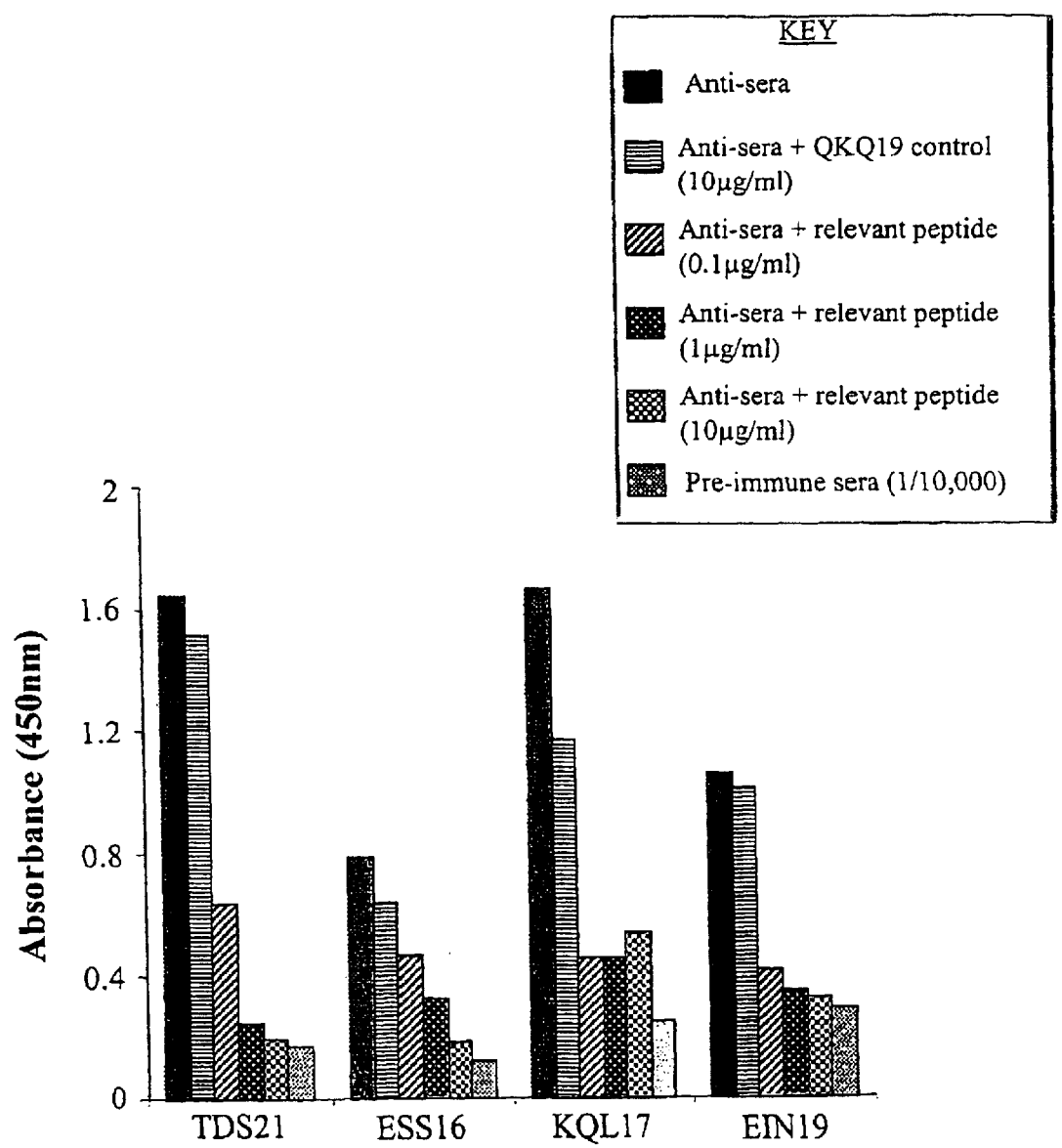
FIG. 6. Plots the results of MtsA peptide blocking of sheep anti-MtsA peptide antisera ELISA against plates coated with MtsA protein.

A further peptide, QDP13, has also been highlighted as a potential vaccine candidate, based on its ability to raise antisera in rabbits which reacts with the MtsA protein (data not shown).

peptide (eight sheep in total). FIG. 5 shows that the anti-peptide antisera also bound to whole MtsA protein, demonstrating the ability of the peptides to raise antisera which may bind to natural protein on cells. That this binding is specific was demonstrated in a peptide blocking ELISA experiment, where peptide was titrated into the sera prior to reacting the sera in an ELISA against whole protein (FIG. 6).

Example 8

Western Blot Analysis

Various strains of *S.pyogenes* were tested by Western Blot, using the sheep anti-TDS 21 antisera to detect the protein. In particular, Western Blots from SDS-PAGE of *S.pyogenes* proteins were incubated with 30 ml 5% (W/V) milk powder/PBS as a blocking solution. 30 µl (1/1000) sheep antiserum (anti-TDS21) was added in 30 ml 5% (W/V) milk powder PBS and incubated for 60 mins at room temperature. After 3 washes, 3.0 µl (1/10000) of donkey anti-sheep IgG peroxidase in 30 µl 5% (W/V) milk powder/PBS was added and incubated for 60 minutes, washed and peroxidase substrate added. All 23 strains had detectable protein.

The results along with the PCR results are set out below.

TABLE 1

MTSA Gene and Protein Distribution in group A *Streptococcus*, as determined by PCR analysis and Western Blot.

| Group A Strain | REF. No | Source | MtsA gene detection | Approximate No. of base pairs | Predicted mol weight of protein | Protein expression (Western Blot) |
| --- | --- | --- | --- | --- | --- | --- |
| M1 | AP-1 | LUND | + | 949.05 | 31.64 | + |
| T11 | AP-74 | LUND | + | 949.05 | 31.64 | + |
| M1 | 3686-98 | CDC | + | 993.51 | 33.12 | + |
| M2 | 3688-98 | CDC | + | TBD | TBD | + |
| M3 | 3671-98 | CDC | + | 943.87 | 31.46 | + |
| M4 | 3670-98 | CDC | + | 943.87 | 31.46 | + |
| M5 | 3667-98 | CDC | + | 890.90 | 29.69 | + |
| M6 | 3693-98 | CDC | + | TBD | TBD | + |
| M9 | 3261-98 | CDC | + | 890.90 | 29.69 | + |
| M11 | 3904-98 | CDC | + | 890.90 | 29.69 | + |
| M12 | 3664-98 | CDC | + | 890.90 | 29.69 | + |
| M18 | 3258-98 | CDC | + | TBD | TBD | + |
| M19 | 3913-98 | CDC | + | 840.90 | 28.03 | + |
| M22 | 3858-98 | CDC | + | 840.90 | 28.03 | + |
| M24 | 55-987 | CDC | + | TBD | TBD | + |
| M28 | 3272-98 | CDC | + | 840.90 | 28.03 | + |
| M49 | 3274-98 | CDC | + | 840.90 | 28.03 | + |
| M55 | 189-98 | CDC | + | TBD | TBD | + |
| M57 | 55-790 | CDC | + | 840.90 | 28.03 | + |
| M60 | 978-97 | CDC | + | 793.70 | 26.45 | + |
| M non typeable | 88/30 | Australia | + | 840.90 | 28.03 | + |
| M6 | 2036 | Australia | + | TBD | TBD | + |
| M12 | 2040 | Australia | + | TBD | TBD | + |

+ means genomic DNA PCR product or protein was detectable,
TBD = to be determined.

Example 9

Immunisation Studies

The Spy-LP-ESS16 peptide was also used to immunize rats. The rats were treated intraperitoneally with a dose volume of 1 ml/animal. Control groups received 1 ml saline, 100 µg keyhole limpet hemocyanin (KLH) in 1 ml saline, 500 µl of Freund's complete adjuvant (FCA) plus 500 µl saline or 1 mg aluminum hydroxide in 1 ml total volume. Peptide was administered at 100 µg/ml. Rats were given a boost on day 21 and bled on day 42. Plates were coated with peptide at 5 µg/ml in carbonate buffer. Serum was titrated against the peptide in 10 fold dilutions from 1 in 100 in PBS and binding detected using an anti-rat HRP conjugate and T1 substrate. To summarize this data, the control sera, sera from rats injected with free peptide in the absence of adjuvant, sera from rats injected with free peptide in FCA, and sera from rats injected with free peptide in alhydrogel (alum) did not react to the ESS16 peptide bound to plates. In contrast, sera from rats injected with peptide KLH conjugates or peptide KLH conjugates in alum or CFA all contained substantial antibody titres.

Example 10

Analysis of Natural Human Immunity

The TDS21 peptide was chosen for further studies of endemic human immunity. Free TDS21 peptide was coated onto ELISA plates and reacted with sera obtained from Thai volunteers. The Thai population under study has a high prevalence of infection with GAS, and a high incidence of rheumatic heart disease (RHD). Normal and RHD responses were compared. The results showed clearly that both normal and RHD sera may contain antibodies to TDS21, and in fact the incidence of such antibodies appears to be higher in the normal population (data not shown). Thus, the TDS21 epitope is recognized during natural exposure to GAS.

Similarly, the TDS21 and QDP13 peptides were used to stimulate lymphocytes from the same Thai individuals. As with antibodies, the TDS21 response was more common in the control than the RHD population. QDP13 stimulated only cells from RHD individuals.

What is claimed is:

1. An isolated and purified polypeptide which comprises:

(a) the amino acid sequence of SEQ ID NO:2, (b) an amino acid sequence having at least 95% identity to SEQ ID NO:2 and which specifically binds an antibody which binds specifically to a MtsA polypeptide having the amino acid sequence of SEQ ID NO:2, or (c) an immunogenic fragment of the amino acid sequence of SEQ ID NO:2, wherein the fragment is at least 60 amino acids in length, the at least 60 amino acids are contiguous amino acids in SEQ ID NO:2, and the fragment specifically binds an antibody which binds specifically to a MtsA polypeptide having the amino acid sequence of SEQ ID NO:2.

2. A composition which invokes an immune response to a *Streptococcus*, comprising a pharmaceutically acceptable carrier and an immunogenically effective amount of an isolated and purified polypeptide which comprises:

(a) the amino acid sequence of SEQ ID NO:2, (b) an amino acid sequence having at least 95% identity to SEQ ID NO:2 and which generates an immune response to a *Streptococcus*, or (c) an immunogenic fragment of the amino acid sequence of SEQ ID NO:2, wherein the fragment is of at least 60 amino acids in length, the at least 60 amino acids are contiguous amino acids in SEQ ID NO:2, and the fragment generates an immune response against a *Streptococcus*.

3. A composition according to claim 2, wherein the *Streptococcus* is a group A *Streptococcus*.

4. A method of invoking an immune response in a host to a *Streptococcus*, comprising administering to the host an effective amount of an isolated and purified polypeptide which comprises:

(a) the amino acid sequence of SEQ ID NO:2, (b) an amino acid sequence having at least 95% identity to SEQ ID NO:2 and which specifically binds an antibody which binds specifically to a MtsA polypeptide having the amino acid sequence of SEQ ID NO:2, or (c) an immunogenic fragment of the amino acid sequence of SEQ ID NO:2, wherein the fragment is at least 60 amino acids in length, the at least 60 amino acids are contiguous amino acids in SEQ ID NO:2, and the fragment specifically binds an antibody which binds specifically to a MtsA polypeptide having the amino acid sequence of SEQ ID NO:2.

5. An isolated and purified polypeptide according to claim 1, wherein the polypeptide comprises the amino acid sequence of SEQ ID NO:2.

6. An isolated and purified polypeptide according to claim 1, wherein the polypeptide comprises an amino acid sequence having at least 95% identity to SEQ ID NO:2 and which specifically binds an antibody which binds specifically to a MtsA polypeptide having the amino acid sequence of SEQ ID NO:2.

7. An isolated and purified polypeptide according to claim 1, wherein the polypeptide comprises an immunogenic fragment of the amino acid sequence of SEQ ID NO:2, wherein the fragment is at least 60 amino acids in length, the at least 60 amino acids are contiguous amino acids in SEQ ID NO:2, and the fragment specifically binds an antibody which binds specifically to a MtsA polypeptide having the amino acid sequence of SEQ ID NO:2.

8. A composition according to claim 2, wherein the polypeptide comprises the amino acid sequence of SEQ ID NO:2.

9. A composition according to claim 2, wherein the polypeptide comprises an amino acid sequence having at least 95% identity to SEQ ID NO:2 and which specifically binds an antibody which binds specifically to a MtsA polypeptide having the amino acid sequence of SEQ ID NO:2.

10. A composition according to claim 2, wherein the polypeptide comprises an immunogenic fragment of the amino acid sequence of SEQ ID NO:2, wherein the fragment is at least 60 amino acids in length, the at least 60 amino acids are contiguous amino acids in SEQ ID NO:2, and the fragment specifically binds an antibody which binds specifically to a MtsA polypeptide having the amino acid sequence of SEQ ID NO:2.

11. A method according to claim 4, wherein the polypeptide comprises the amino acid sequence of SEQ ID NO:2.

12. A method according to claim 4, wherein the polypeptide comprises an amino acid sequence having at least 95% identity to SEQ ID NO:2 and which specifically binds an antibody which binds specifically to a MtsA polypeptide having the amino acid sequence of SEQ ID NO:2.

13. A method according to claim 4, wherein the polypeptide comprises an immunogenic fragment of the amino acid sequence of SEQ ID NO:2, wherein the fragment is at least 60 amino acids in length, the at least 60 amino acids are contiguous amino acids in SEQ ID NO:2, and the fragment specifically binds an antibody which binds specifically to a MtsA polypeptide having the amino acid sequence of SEQ ID NO:2.

14. A method according to claim 4, wherein the *Streptococcus* is a group A *Streptococcus*.

* * * * *